(12) United States Patent
Lele et al.

(10) Patent No.: US 7,332,597 B2
(45) Date of Patent: Feb. 19, 2008

(54) PRIMERS AND PROBE TO IDENTIFY MYCOBACTERIUM TUBERCULOSIS COMPLEX

(75) Inventors: Subodh M. Lele, Lexington, KY (US); Manjiri S. Lele, Lexington, KY (US); Nada H. Khattar, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 10/876,756

(22) Filed: Jun. 28, 2004

(65) Prior Publication Data
US 2005/0287534 A1 Dec. 29, 2005

(51) Int. Cl.
*C07H 21/04* (2006.01)
*C07H 21/02* (2006.01)
*C07H 21/00* (2006.01)

(52) U.S. Cl. .................. 536/23.7; 536/23.1; 536/24.3; 536/24.32; 536/24.33; 536/25.6

(58) Field of Classification Search ............... 536/23.1, 536/23.7, 24.3, 24.32, 24.33, 25.6
See application file for complete search history.

(56) References Cited

U.S. PATENT DOCUMENTS

| | | | |
|---|---|---|---|
| 5,712,095 A | 1/1998 | Britschgi et al. |
| 5,726,021 A | 3/1998 | Britschgi et al. |
| 6,197,584 B1 | 3/2001 | Bennett et al. |
| 6,312,903 B1 | 11/2001 | Jannes et al. |
| 6,428,963 B2 | 8/2002 | Danenberg et al. |
| 2003/0104410 A1 | 6/2003 | Mittmann |
| 2003/0228597 A1 | 12/2003 | Cowsert et al. |
| 2003/0235893 A1 | 12/2003 | Weigel et al. |

FOREIGN PATENT DOCUMENTS

| | | |
|---|---|---|
| CN | 1326973 | 12/2001 |
| CN | 1328023 A | 12/2001 |
| CN | 1329077 A | 1/2002 |
| CN | 1333218 A | 1/2002 |
| EP | 0 298 807 B1 | 1/1989 |
| EP | 1 091 004 A2 | 4/2001 |
| JP | 2002-511276 A | 4/2002 |
| JP | 2002-513593 A | 5/2002 |
| WO | WO 96/00298 | 1/1996 |
| WO | WO 99/57320 | 11/1999 |
| WO | WO 00/58519 | 10/2000 |
| WO | WO 00/73436 A1 | 12/2000 |
| WO | WO 01/72796 A1 | 10/2001 |
| WO | WO 02/22872 A1 | 3/2002 |
| WO | WO 02/057414 A2 | 7/2002 |
| WO | WO 03/003165 A2 | 1/2003 |
| WO | WO 03/025176 A2 | 3/2003 |
| WO | WO 03/031654 A1 | 4/2003 |
| WO | WO 03/035894 A2 | 5/2003 |
| WO | WO 03/035895 A2 | 5/2003 |
| WO | WO 03/037247 A2 | 5/2003 |
| WO | WO 048330 A2 | 6/2003 |
| WO | WO 03/054143 A2 | 7/2003 |

OTHER PUBLICATIONS

Lele M.S., Khattar N.H., Shajahan S., Ahmed M., Ribes J., Lele S.M. A real-time quantitative PCR assay for specific identification of *Mycobacterium tuberculosis* complex in formalin-fixed paraffin-embedded tissue sections. Presented at the Annual Meeting of the United States and Canadian Academy of Pathology, Mar. 2004. Abstract published in *Laboratory Investigation* 2004;84:281A (abstract).
Park et al., Arch Pathol Lab Med, vol. 127, Apr. 2003, pp. 451-455.
Brisson-Noel et al., Lancet 1989; 2:1069-1071.
Beige et al., J.Clin. Microbiol. 1995; 33:90-95.
Perosio et al., Am.J.Clin.Pathol. 1993; 100:643-647.
Hardman et al., Am.J.Clin.Pathol. 1996; 106:384-389.
Salian et al., Am.J.Respir.Crit.Care Med. 1998;158:1150-1155.
Vago et al., Am.J.Clin.Pathol. 1998;109:411-415.
Heid et al., Genome Res 1996;6:986-994.
Gibson et al. Genome Res 1996;6:995-1001.
CAS Registry No. 205703-48-6.
Genbank AV834508.
Genbank AZ309027.
CAS Registry No. 470725-24-7.
CAS Registry No. 344806-98-0.
CAS Registry No. 215243-93-9.
Genbank BH865290.

*Primary Examiner*—Rodney P Swartz
(74) *Attorney, Agent, or Firm*—McDermott Will & Emery LLP

(57) ABSTRACT

Methods and nucleic acids for rapid, reliable and sensitive detection of *Mycobacterium tuberculosis* (MTB) complex pathogen in a biological sample. Oligonucleotides are provided which amplify MTB DNA and which are useful in carrying out real time PCR of DNA obtained from formalin-fixed and paraffin-embedded tissue samples.

10 Claims, 5 Drawing Sheets

Figure 1:
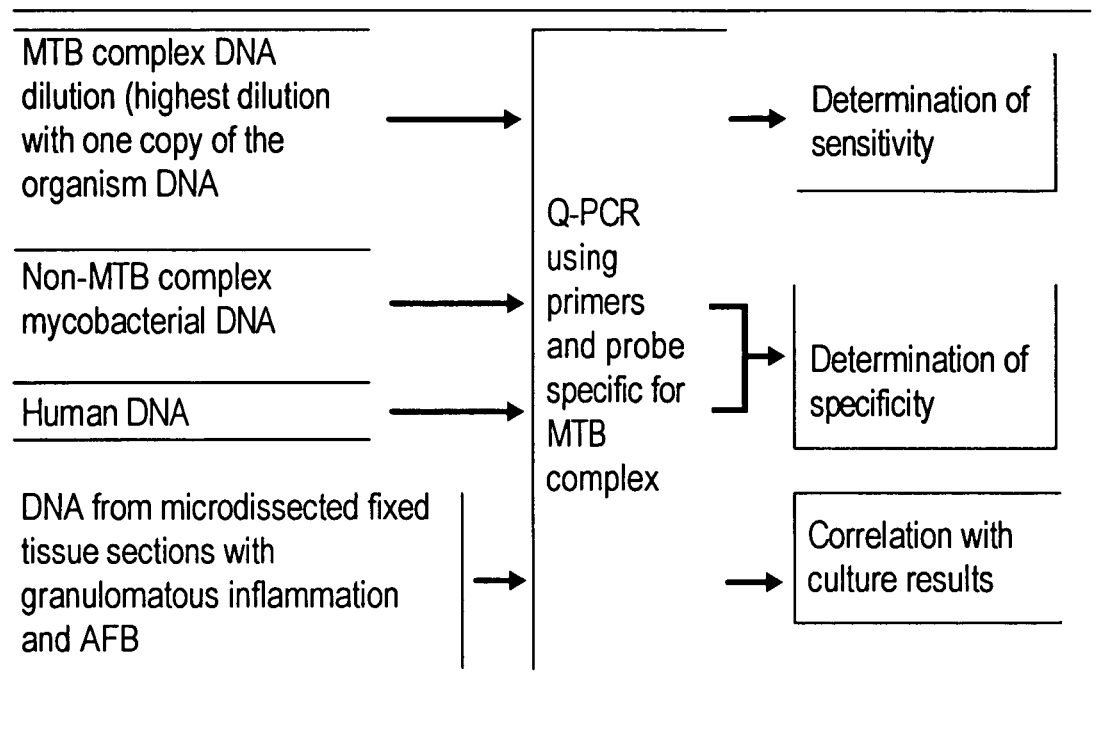
Figure 2:
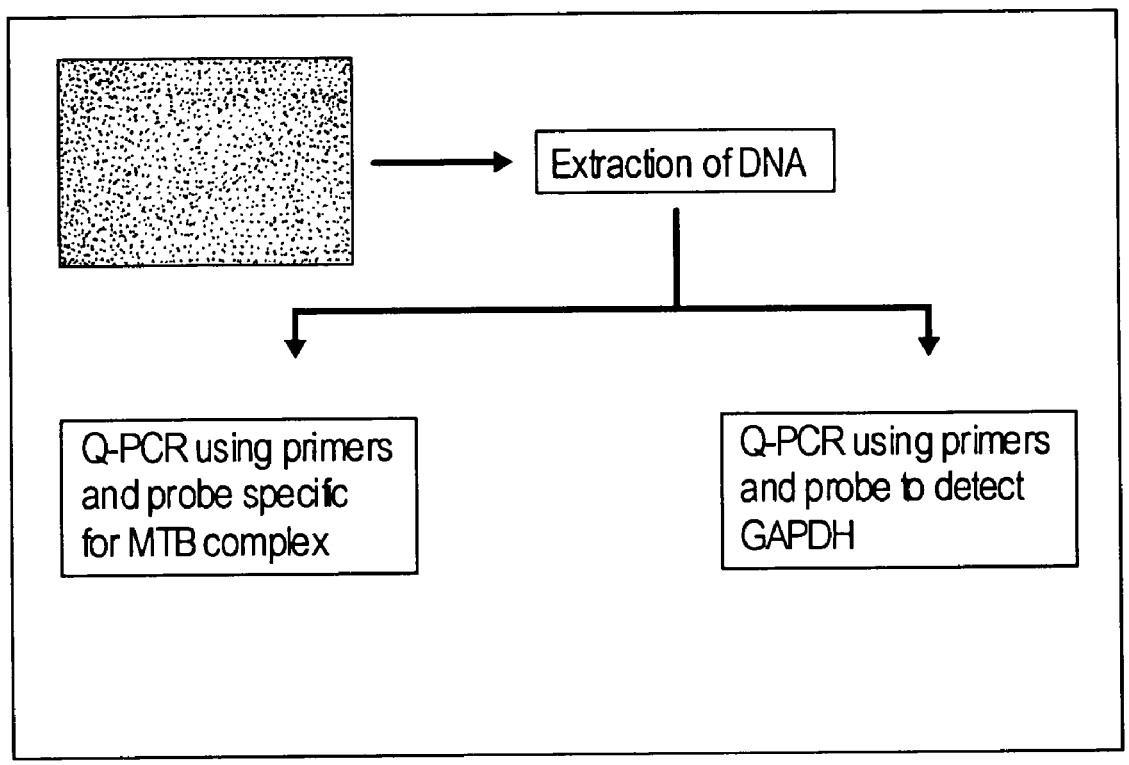
Figure 3:
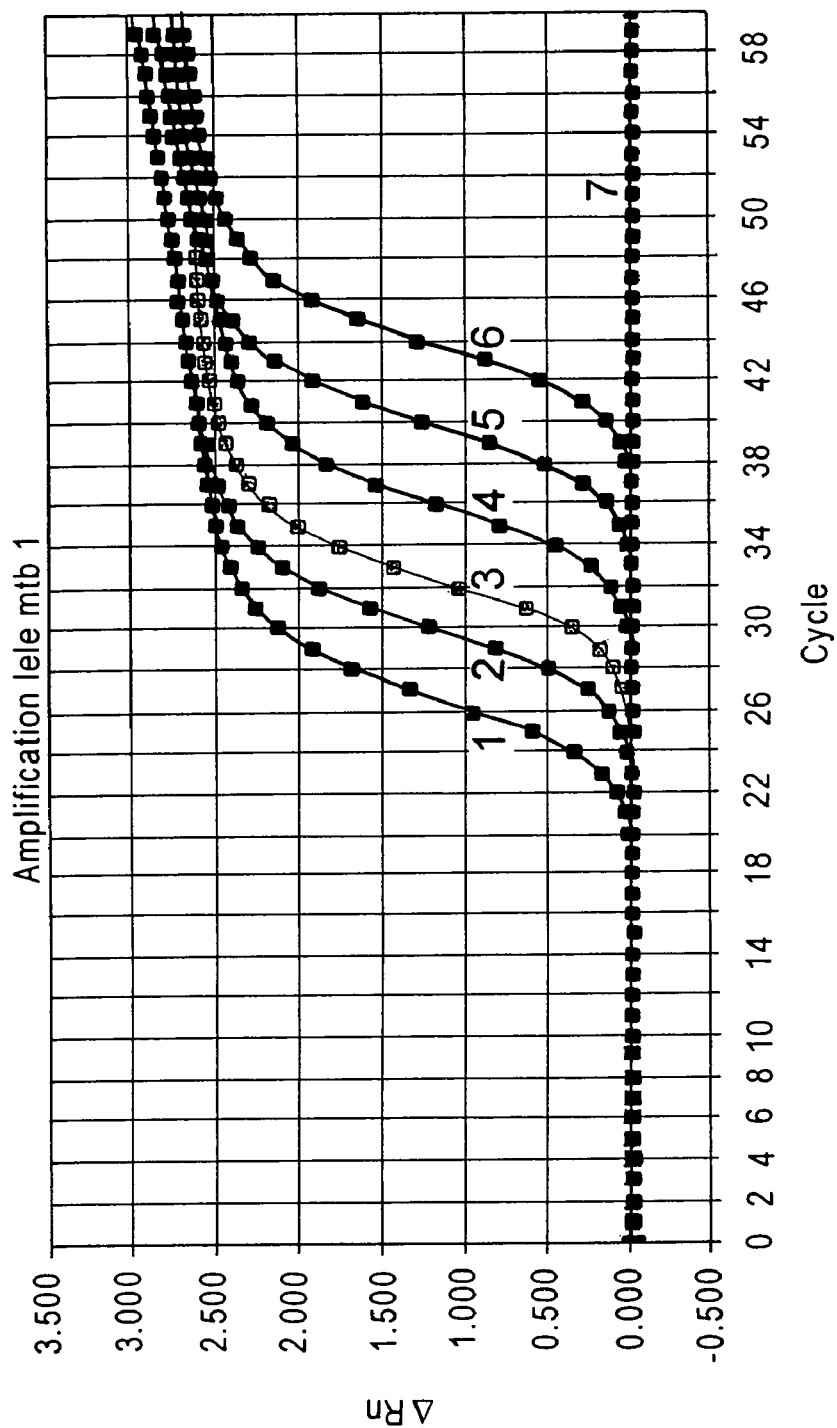
Figure 4:
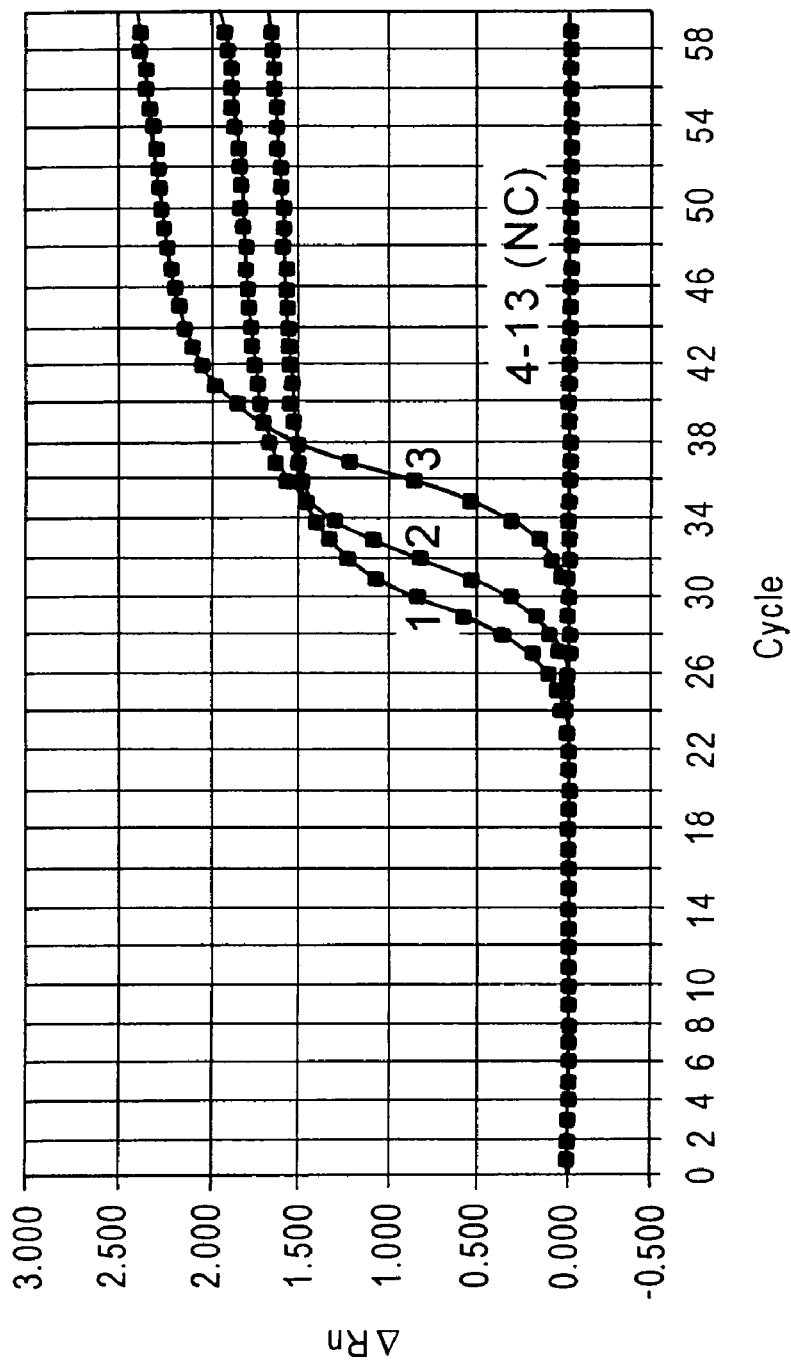

Experimental design. MTB: Mycobacterium tuberculosis; PCR: Polymerase chain reaction; AFB: acid-fast bacilli Real-time procedure performed on microdissected FFPE tissue sections Q-PCR using MTB complex specific primers and probe performed on atypical mycobacteria (*M. marinum, M. avium, M. cheloneae, M. intracellulare, M. kansasii, M. fortuitum, M. cheloneae* subspecies *abscessus, M. terrae, M. gordonae*) and human DNA used as negative controls (NC), and DNA from cases 1-3 (Figure 5) that show a positive result.

| Case | Real-time PCR | Culture |
| --- | --- | --- |
| 1 | MTB complex | MTB complex |
| 2 | MTB complex | MTB complex |
| 3 | MTB complex | MTB complex |
| 4 | Negative | MAI |
| 5 | Negative | MAI |
| 6 | Negative | M. fortuitum |
| 7 | Negative | M. fortuitum |

MTB complex: *Mycobacterium tuberculosis complex;*
MAI; *Mycobacterium avium intracellulare*

Correlation of Q-PCR results on FFPE tissue sections positive for acid-fast bacilli and identification of the organism by culture

Figure 5

SEQUENCE LISTING

```
<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: Chemically synthesized

<400> SEQUENCE: 1
gacaacaaag ttggccacca                                                  20

<210> SEQ ID NO 2
<211> LENGTH: 20
<212> TYPE: DNA
<213> ORGANISM: Artificial Sequence
<220> FEATURE:
<223> OTHER INFORMATION: Chemically synthesized

<400> SEQUENCE: 2
tgggacaaca cctggaacaa                                                  20

<210> SEQ ID NO 3
<211> LENGTH: 23
<212> TYPE: DNA
<213> ORGANISM: Artificial Sequence
<220> FEATURE:
<223> OTHER INFORMATION: Chemically synthesized

<400> SEQUENCE: 3
ttgggtcctg aggcaacact cgg                                              23
```

```
<210> SEQ ID NO 4
<211> LENGTH: 18
<212> TYPE: DNA
<213> ORGANISM: Artificial Sequence
<220> FEATURE:
<223> OTHER INFORMATION: Chemically synthesized

<400> SEQUENCE: 4
gacaacaaag ttggccac                                                 18

<210> SEQ ID NO 5
<211> LENGTH: 18
<212> TYPE: DNA
<213> ORGANISM: Artificial Sequence
<220> FEATURE:
<223> OTHER INFORMATION: Chemically synthesized

<400> SEQUENCE: 5
caacaaagtt ggccacca                                                 18

<210> SEQ ID NO 6
<211> LENGTH: 16
<212> TYPE: DNA
<213> ORGANISM: Artificial Sequence
<220> FEATURE:
<223> OTHER INFORMATION: Chemically synthesized

<400> SEQUENCE: 6
caacaaagtt ggccac                                                   16

<210> SEQ ID NO 7
<211> LENGTH: 18
<212> TYPE: DNA
<213> ORGANISM: Artificial Sequence
<220> FEATURE:
<223> OTHER INFORMATION: Chemically synthesized

<400> SEQUENCE: 7
acaacaaagt tggccacc                                                 18

<210> SEQ ID NO 8
<211> LENGTH: 19
<212> TYPE: DNA
<213> ORGANISM: Artificial Sequence
<220> FEATURE:
<223> OTHER INFORMATION: Chemically synthesized

<400> SEQUENCE: 8
acaacaaagt tggccacca                                                19

<210> SEQ ID NO 9
<211> LENGTH: 19
<212> TYPE: DNA
<213> ORGANISM: Artificial Sequence
<220> FEATURE:
<223> OTHER INFORMATION: Chemically synthesized

<400> SEQUENCE: 9
gacaacaaag ttggccacc                                                19

<210> SEQ ID NO 10
<211> LENGTH: 17
<212> TYPE: DNA
<213> ORGANISM: Artificial Sequence
<220> FEATURE:
```

-continued

<223> OTHER INFORMATION: Chemically synthesized

<400> SEQUENCE: 10
caacaaagtt ggccacc                                                    17

<210> SEQ ID NO 11
<211> LENGTH: 17
<212> TYPE: DNA
<213> ORGANISM: Artificial Sequence
<220> FEATURE:
<223> OTHER INFORMATION: Chemically synthesized

<400> SEQUENCE: 11
acaacaaagt tggccac                                                    17

<210> SEQ ID NO 12
<211> LENGTH: 21
<212> TYPE: DNA
<213> ORGANISM: Artificial Sequence
<220> FEATURE:
<223> OTHER INFORMATION: Chemically synthesized

<400> SEQUENCE: 12
tgacaacaaa gttggccacc a                                               21

<210> SEQ ID NO 13
<211> LENGTH: 21
<212> TYPE: DNA
<213> ORGANISM: Artificial Sequence
<220> FEATURE:
<223> OTHER INFORMATION: Chemically synthesized

<400> SEQUENCE: 13
gacaacaaag ttggccacca a                                               21

<210> SEQ ID NO 14
<211> LENGTH: 26
<212> TYPE: DNA
<213> ORGANISM: Artificial Sequence
<220> FEATURE:
<223> OTHER INFORMATION: Chemically synthesized

<400> SEQUENCE: 14
gaattcgaca acaaagttgg ccacca                                          26

<210> SEQ ID NO 15
<211> LENGTH: 18
<212> TYPE: DNA
<213> ORGANISM: Artificial Sequence
<220> FEATURE:
<223> OTHER INFORMATION: Chemically synthesized

<400> SEQUENCE: 15
tgggacaaca cctggaac                                                   18

<210> SEQ ID NO 16
<211> LENGTH: 18
<212> TYPE: DNA
<213> ORGANISM: Artificial Sequence
<220> FEATURE:
<223> OTHER INFORMATION: Chemically synthesized

<400> SEQUENCE: 16
ggacaacacc tggaacaa                                                   18

```
<210> SEQ ID NO 17
<211> LENGTH: 16
<212> TYPE: DNA
<213> ORGANISM: Artificial Sequence
<220> FEATURE:
<223> OTHER INFORMATION: Chemically synthesized

<400> SEQUENCE: 17
ggacaacacc tggaac                                                    16

<210> SEQ ID NO 18
<211> LENGTH: 18
<212> TYPE: DNA
<213> ORGANISM: Artificial Sequence
<220> FEATURE:
<223> OTHER INFORMATION: Chemically synthesized

<400> SEQUENCE: 18
gggacaacac ctggaaca                                                  18

<210> SEQ ID NO 19
<211> LENGTH: 19
<212> TYPE: DNA
<213> ORGANISM: Artificial Sequence
<220> FEATURE:
<223> OTHER INFORMATION: Chemically synthesized

<400> SEQUENCE: 19
gggacaacac ctggaacaa                                                 19

<210> SEQ ID NO 20
<211> LENGTH: 19
<212> TYPE: DNA
<213> ORGANISM: Artificial Sequence
<220> FEATURE:
<223> OTHER INFORMATION: Chemically synthesized

<400> SEQUENCE: 20
tgggacaaca cctggaaca                                                 19

<210> SEQ ID NO 21
<211> LENGTH: 17
<212> TYPE: DNA
<213> ORGANISM: Artificial Sequence
<220> FEATURE:
<223> OTHER INFORMATION: Chemically synthesized

<400> SEQUENCE: 21
ggacaacacc tggaaca                                                   17

<210> SEQ ID NO 22
<211> LENGTH: 17
<212> TYPE: DNA
<213> ORGANISM: Artificial Sequence
<220> FEATURE:
<223> OTHER INFORMATION: Chemically synthesized

<400> SEQUENCE: 22
gggacaacac ctggaac                                                   17

<210> SEQ ID NO 23
<211> LENGTH: 21
<212> TYPE: DNA
<213> ORGANISM: Artificial Sequence
<220> FEATURE:
<223> OTHER INFORMATION: Chemically synthesized
```

```
<400> SEQUENCE: 23
gtgggacaac acctggaaca a                                              21

<210> SEQ ID NO 24
<211> LENGTH: 21
<212> TYPE: DNA
<213> ORGANISM: Artificial Sequence
<220> FEATURE:
<223> OTHER INFORMATION: Chemically synthesized

<400> SEQUENCE: 24
tgggacaaca cctggaacaa g                                              21

<210> SEQ ID NO 25
<211> LENGTH: 26
<212> TYPE: DNA
<213> ORGANISM: Artificial Sequence
<220> FEATURE:
<223> OTHER INFORMATION: Chemically synthesized

<400> SEQUENCE: 25
gaattctggg acaacacctg gaacaa                                         26

<210> SEQ ID NO 26
<211> LENGTH: 21
<212> TYPE: DNA
<213> ORGANISM: Artificial Sequence
<220> FEATURE:
<223> OTHER INFORMATION: Chemically synthesized

<400> SEQUENCE: 26
ttgggtcctg aggcaacact c                                              21

<210> SEQ ID NO 27
<211> LENGTH: 21
<212> TYPE: DNA
<213> ORGANISM: Artificial Sequence
<220> FEATURE:
<223> OTHER INFORMATION: Chemically synthesized

<400> SEQUENCE: 27
gggtcctgag gcaacactcg g                                              21

<210> SEQ ID NO 28
<211> LENGTH: 19
<212> TYPE: DNA
<213> ORGANISM: Artificial Sequence
<220> FEATURE:
<223> OTHER INFORMATION: Chemically synthesized

<400> SEQUENCE: 28
gggtcctgag gcaacactc                                                 19

<210> SEQ ID NO 29
<211> LENGTH: 21
<212> TYPE: DNA
<213> ORGANISM: Artificial Sequence
<220> FEATURE:
<223> OTHER INFORMATION: Chemically synthesized

<400> SEQUENCE: 29
tgggtcctga ggcaacactc g                                              21

<210> SEQ ID NO 30
<211> LENGTH: 22
```

```
<210> SEQ ID NO 30
<211> LENGTH: 22
<212> TYPE: DNA
<213> ORGANISM: Artificial Sequence
<220> FEATURE:
<223> OTHER INFORMATION: Chemically synthesized

<400> SEQUENCE: 30
tgggtcctga ggcaacactc gg                                              22

<210> SEQ ID NO 31
<211> LENGTH: 22
<212> TYPE: DNA
<213> ORGANISM: Artificial Sequence
<220> FEATURE:
<223> OTHER INFORMATION: Chemically synthesized

<400> SEQUENCE: 31
ttgggtcctg aggcaacact cg                                              22

<210> SEQ ID NO 32
<211> LENGTH: 20
<212> TYPE: DNA
<213> ORGANISM: Artificial Sequence
<220> FEATURE:
<223> OTHER INFORMATION: Chemically synthesized

<400> SEQUENCE: 32
gggtcctgag gcaacactcg                                                 20

<210> SEQ ID NO 33
<211> LENGTH: 20
<212> TYPE: DNA
<213> ORGANISM: Artificial Sequence
<220> FEATURE:
<223> OTHER INFORMATION: Chemically synthesized

<400> SEQUENCE: 33
tgggtcctga ggcaacactc                                                 20

<210> SEQ ID NO 34
<211> LENGTH: 24
<212> TYPE: DNA
<213> ORGANISM: Artificial Sequence
<220> FEATURE:
<223> OTHER INFORMATION: Chemically synthesized

<400> SEQUENCE: 34
gttgggtcct gaggcaacac tcgg                                            24

<210> SEQ ID NO 35
<211> LENGTH: 24
<212> TYPE: DNA
<213> ORGANISM: Artificial Sequence
<220> FEATURE:
<223> OTHER INFORMATION: Chemically synthesized

<400> SEQUENCE: 35
ttgggtcctg aggcaacact cgga                                            24

<210> SEQ ID NO 36
<211> LENGTH: 15
<212> TYPE: DNA
<213> ORGANISM: Artificial Sequence
<220> FEATURE:
<223> OTHER INFORMATION: Chemically synthesized

<400> SEQUENCE: 36
```

-continued

```
caacaaagtt ggcca                                                    15

<210> SEQ ID NO 37
<211> LENGTH: 20
<212> TYPE: DNA
<213> ORGANISM: Artificial Sequence
<220> FEATURE:
<223> OTHER INFORMATION: Chemically synthesized

<400> SEQUENCE: 37
catgacaaca aagttggcca                                               20

<210> SEQ ID NO 38
<211> LENGTH: 20
<212> TYPE: DNA
<213> ORGANISM: Artificial Sequence
<220> FEATURE:
<223> OTHER INFORMATION: Chemically synthesized

<400> SEQUENCE: 38
ggtgggacaa cacctggaac                                               20

<210> SEQ ID NO 39
<211> LENGTH: 12
<212> TYPE: DNA
<213> ORGANISM: Artificial Sequence
<220> FEATURE:
<223> OTHER INFORMATION: Chemically synthesized

<400> SEQUENCE: 39
acaacacctg ga                                                       12

<210> SEQ ID NO 40
<211> LENGTH: 12
<212> TYPE: DNA
<213> ORGANISM: Artificial Sequence
<220> FEATURE:
<223> OTHER INFORMATION: Chemically synthesized

<400> SEQUENCE: 40
caacacctgg aa                                                       12
```

PRIMERS AND PROBE TO IDENTIFY MYCOBACTERIUM TUBERCULOSIS COMPLEX

FIELD OF THE INVENTION

Methods and nucleic acids are disclosed for rapid, reliable, simple and highly sensitive detection of DNA of the *Mycobacterium tuberculosis* (MTB) complex with quantitative real time PCR in formalin-fixed tissues.

BACKGROUND OF THE INVENTION

Rapid identification of microbial pathogens has long been an important goal of diagnostic technology. In addition to identifying the pathogenic species, the clinician must now affirm the potential efficacy of standard antimicrobial treatments early in the treatment of each case. Delays and erroneous results associated with conventional diagnostic tests frequently lead to the administration of ineffective treatments, which in turn lead to complications, added costs, and poor outcomes.

Tuberculosis (TB) kills 3,000,000 people in the world every year, more than AIDS, malaria, and other tropical diseases combined. One third of the world's population is infected with tuberculosis and it represents more than a quarter of the world's preventable deaths. The responsible mycobacteria are Gram-positive (no outer cell membrane), non-motile, pleomorphic rods, related to Actinomyces.

Organisms of the *Mycobacterium tuberculosis* (MTB) complex are responsible for the significant TB-associated morbidity and mortality observed in humans. The TB complex consists of the following species: *M. tuberculosis, M. bovis, M. bovis BCG, M. africanum, M. microti,* and *M. canetti. M. tuberculosis* is the most common MTB complex pathogen isolated in humans. *M. bovis BCG* may be transmitted from infected animals to humans, *M. africanum* causes pulmonary tuberculosis in tropical Africa and *M. microti* primarily infects animals.

Tuberculosis is highly contagious, therefore rapid diagnosis of the disease is important. Classical methods for identification of mycobacteria rely on staining specimens for acid fast bacilli followed by culture and biochemical testing. These cumbersome techniques render the identification and quantification of MTB complex pathogen very inefficient.

Therefore, although there are reports of PCR-based tests for diagnosis of TB, there is a continuing need for highly sensitive assays to rapidly detect the organisms causing TB. See Park et al., Arch Pathol Lab Med, Vol. 127, March 2003, pp. 326-330; Brisson-Noel et al., Lancet 1989; 2:1069-1071; Beige et al., J. Clin. Microbiol. 1995; 33:90-95; Perosio et al., Am. J. Clin. Pathol. 1993; 100:643-647; Hardman et al., Am. J. Clin. Pathol. 1996; 106:384-389; Salian et al., Am. J. Respir. Crit. Care Med. 1998; 158:1150-1155; Vago et al., Am. J. Clin. Pathol. 1998; 109:411-415.

All articles and patent documents cited herein are expressly incorporated by reference for their entirety for all purposes.

SUMMARY OF THE INVENTION

One aspect of the invention relates to an isolated oligonucleotide of the sequence SEQ ID NO: 1.

Another aspect of the invention relates to an isolated oligonucleotide that hybridizes the complement of SEQ ID NO: 1 under stringent conditions and is capable of amplifying MTB complex DNA when used in conjunction with SEQ ID NO: 2 in a polymerase chain reaction.

Another aspect of the invention relates to an isolated oligonucleotide of the sequence of SEQ ID NO: 1, wherein from about one to about three nucleotides are added or removed from the 5' end and/or from about one to about three nucleotides are added or removed from the 3' end, respectively, and wherein the oligonucleotide is capable of amplifying MTB complex DNA when used in conjunction with SEQ ID NO: 2 in a polymerase chain reaction.

Another aspect of the invention relates to an isolated oligonucleotide of the sequence SEQ ID NO: 2.

Another aspect of the invention relates to an isolated oligonucleotide that hybridizes the complement of SEQ ID NO: 2 under stringent conditions and is capable of amplifying MTB complex DNA when used in conjunction with SEQ ID NO: 1 in a polymerase chain reaction.

Another aspect of the invention relates to an isolated oligonucleotide of the sequence of SEQ ID NO: 2, wherein from about one to about three nucleotides are added or removed from the 5' end and/or from about one to about three nucleotides are added or removed from the 3' end, respectively, and wherein the oligonucleotide is capable of amplifying MTB complex DNA when used in conjunction with SEQ ID NO: 1 in a polymerase chain reaction.

Another aspect of the invention relates to an isolated oligonucleotide having the sequence of SEQ ID NO: 3 or a sequence wherein about one to about three nucleotides are added or removed from the 5' end and/or about one to about three nucleotides are added or removed from the 3' end of SEQ ID NO: 3.

Another aspect of the invention relates to a kit for detecting MTB complex DNA comprising a first isolated oligonucleotide of SEQ ID NO: 1 or an oligonucleotide substantially identical thereto and a second oligonucleotide of SEQ ID NO: 2 or an oligonucleotide substantially identical thereto. In one embodiment of this aspect of the invention the kit further comprises oligonucleotide of the sequence of SEQ ID No: 3 or a sequence substantially identical thereto.

Another aspect of the invention relates to a method of detecting the presence of MTB complex DNA in a biological sample comprising; obtaining a biological sample from an organism; isolating nucleic acids from the sample; performing a polymerase chain reaction on the isolated nucleic acids using as a forward primer SEQ ID NO: 1 or an oligonucleotide substantially identical thereto and as a reverse primer SEQ ID NO: 2 or an oligonucleotide substantially identical thereto; and correlating a presence of an amplification product from the polymerase chain reaction with the presence of MTB complex DNA in the sample.

Another aspect of the invention relates to an method of identifying compounds capable of inhibiting growth of MTB complex pathogen comprising: infecting a tissue culture with an MTB complex pathogen to obtain an infected tissue culture; contacting a portion of the infected tissue culture with a compound suspected of being capable of inhibiting MTB complex pathogen growth; isolating nucleic acids from the portion of the infected tissue culture contacted by the compound to obtain a first nucleic acid sample and from a portion of the remainder of the infected tissue culture not contacted by the compound to obtain a second nucleic acid sample; performing polymerase chain reaction on the first and the second nucleic acid samples using as a forward primer SEQ ID NO: 1 or an oligonucleotide substantially identical thereto and as a reverse primer SEQ ID NO: 2 or an oligonucleotide substantially identical thereto;

whereby a decrease in an amplification product in the first nucleic acid sample relative to the second nucleic acid sample indicates that the compound is capable of inhibiting MTB complex pathogen growth.

BRIEF DESCRIPTION OF THE DRAWINGS

FIG. 1. Schematic representation of the study design. MTB: *Mycobacterium tuberculosis*; PCR: polymerase chain reaction; AFB: acid-fast bacilli.

FIG. 2. Schematic representation of real-time procedure performed on microdissected formalin-fixed paraffin embedded (FFPE) tissue sections.

FIG. 3. Q-PCR using MTB complex specific primers and probe performed on serial dilutions of formalin-fixed MTB DNA. 4000 to 0.04 pg—one organism equivalent—of DNA were used (curves 1-6) as well as a negative control (curve 7).

FIG. 4. Q-PCR using MTB complex specific primers and probe performed on atypical mycobacteria (*M. marinum, M. avium, M. cheloneae, M. intracellulare, M. kansasii, M. fortuitum, M. cheloneae* subspecies *abscessus, M. terrae, M. gordonae*) and human DNA used as negative controls (NC), and DNA from cases 1-3 in FIG. 5, that show a positive result.

FIG. 5. Correlation of Q-PCR results on FFPE tissue sections positive for acid-fast bacilli and identification of the organism by culture.

DETAILED DESCRIPTION OF THE INVENTION

The invention relates to oligonucleotides and methods for the detection of *Mycobacterium tuberculosis* complex (MTB) pathogen in a biological sample. Specifically, the oligonucleotides disclosed herein are useful for the amplification of MTB DNA in biological samples, particularly in real-time polymerase chain reactions (PCR) performed on DNA isolated from formalin-fixed and paraffin-embedded tissue samples. The oligonucleotides and methods disclosed herein are superior to those of the prior art because, for example, they enable the skilled artisan to detect a single copy of MTB complex DNA in a biological sample.

"Nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

The term "oligonucleotide" refers to a molecule comprised of two or more deoxyribonucleotides or ribonucleotides, such as primers, probes, nucleic acid fragments to be detected, and nucleic acid controls. The exact size of an oligonucleotide depends on many factors and the ultimate function or use of the oligonucleotide.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from about 10 to about 30 nucleotides. Short primer molecules generally require cooler temperatures to form sufficiently stable hybrid complexes with the template. A primer need not reflect the exact sequence of the template but must be sufficiently complementary to specifically hybridize with a template. When primer pairs are referred to herein, the pair is meant to include one forward primer which is capable of hybridizing to the sense strand of a double-stranded target nucleic acid (the "sense primer") and one reverse primer which is capable of hybridizing to the antisense strand of a double-stranded target nucleic acid (the "antisense primer").

One aspect of the invention relates to oligonucleotide primers capable of acting as forward primers in a PCR reaction for amplifying MTB complex DNA. Preferably, the forward primer has the sequence: 5'-GACAACAAAGTTGGCCACCA-3' (SEQ ID NO: 1).

Another aspect of the invention relates to oligonucleotide primers capable of acting as reverse primers in a PCR reaction for amplifying MTB complex DNA. Preferably, the reverse primer has the sequence: 5'-TGGGACAACACCTGGAACAA-3' (SEQ ID NO: 2).

Another aspect of the invention relates to oligonucleotide primers capable of acting as a probe for MTB complex DNA. Preferably, the probe has the sequence: 5'-TTGGGTCCTGAGGCAACACTCGG-3' (SEQ ID NO: 3).

"Probe" refers to an oligonucleotide which binds through complementary base pairing to a sub-sequence of a target nucleic acid. A primer may be a probe. It will be understood by one of skill in the art that probes will typically substantially bind target sequences lacking complete complementarity with the probe sequence depending upon the stringency of the hybridization conditions. The probes are typically directly labeled (e.g., with isotopes or fluorescent moieties) or indirectly labeled such as with biotin to which a streptavidin complex may later bind. By assaying for the presence or absence of the probe, one can detect the presence or absence of the target, by Southern blot for example. Preferably, the target is an amplification product generated by PCR amplification of MTB complex nucleic acids using primers SEQ ID NOs: 1 and 2, or oligonucleotides substantially identical thereto, respectively.

More, preferably, the probes are fluorescently labeled and are capable of acting as a hydrolysis or Taqman® probes in a real-time PCR reaction to amplify MTB complex nucleic acids. The real-time PCR method uses a dual labelled fluorogenic oligonucleotide probe (i.e., the hydrolysis or TaqMan® probe) that anneals specifically within the template amplicon spanning the forward (e.g. SEQ ID NO: 1) and reverse primers (e.g. SEQ ID NO: 2). Preferably, a fluorescent reporter molecule attached to 5'-position that fluoresces when released from probe by hydrolytic activity of DNA polymerase. Preferably, a quencher is attached to the 3' end of the probe. A quencher is a fluorescent molecule that quenches (absorbs) the fluorescence emission from the Reporter only when Reporter is attached to the probe before hydrolysis. Preferably, laser stimulation within the capped wells containing the reaction mixture causes emission of a 3' quencher dye (TAMRA) until the probe is cleaved by the 5' to 3' nuclease activity of the DNA polymerase during PCR extension, causing release of a 5' reporter dye (6FAM). Preferably, production of an amplicon causes emission of a fluorescent signal that is detected by a CCD (charge-coupled device) detection camera or other light capturing device, and the amount of signal produced at a threshold cycle within the purely exponential phase of the PCR reaction, reflects the starting copy number of the target sequence being amplified.

The invention also includes oligonucleotides substantially identical to SEQ ID NOs: 1-3. For example, oligonucleotide sequences substantially identical to SEQ ID NOs: 1-3 may have several nucleotides added to or removed from their 5' ends or several nucleotides added to or removed from their 3' ends. "Several nucleotides" in this context refers to about 3 nucleotides, or preferably about two nucleotides or more preferably about one nucleotide. The person of skill in the art will recognize that when adding nucleotides to the 5' and/or 3' ends SEQ ID NOs: 1-3 the identity of those nucleotides may be dictated by the sequence of the MTB complex DNA to be amplified. However, the skilled artisan may also wish to add overhangs to the 5' end of the forward primer or 5' end of the reverse primer (giving a 3' sticky end on the amplicon). Such overhangs may include restriction enzyme sites useful in providing sticky ends to facilitate subcloning of the amplification product, for example.

Primers and probes of the invention exhibit an absence of hybridization to sequences contained in human RNA and DNA. This may be confirmed theoretically by BLAST analysis (NCBI), and empirically by testing selected primer sets against human total nucleic acid under PCR conditions. Additionally, the claims probes and primers lack cross reactivity against other non-MTB complex pathogen genomes that could be present in clinical samples. This may also be confirmed theoretically in a BLAST search, and empirically using genomic material from non-MTB complex pathogen.

For example, one of skill in the art would envisage a genus of sequences substantially identical to SEQ ID NO: 1 wherein about one to about three nucleotides are added or removed from the 5' end and/or about one to about three nucleotides are added or removed from the 3' end, respectively, to include but not be limited to the following exemplary species:

| SEQ ID NO: | Sequence Substantially Identical to SEQ ID NO: 1 | Notes |
|---|---|---|
| 4 | 5'-GACAACAAAGTTGGCCAC-3' | 2 nt removed from '3 end |
| 5 | 5'-CAACAAAGTTGGCCACCA-3' | 2 nt removed from 5' end |
| 6 | 5'-CAACAAAGTTGGCCAC-3' | 2 nt removed from 5' end and 2 nt removed from '3 end |
| 7 | 5'-ACAACAAAGTTGGCCACC-3' | 1 nt removed from 5' end and 1 nt removed from '3 end |
| 8 | 5'-ACAACAAAGTTGGCCACCA-3' | 1 nt removed from 5' end |
| 9 | 5'-GACAACAAAGTTGGCCACC-3' | 1 nt removed from '3 end |
| 10 | 5'-CAACAAAGTTGGCCACC-3' | 2 nt removed from 5' end and 1 nt removed from '3 end |
| 11 | 5'-ACAACAAAGTTGGCCAC-3' | 1 nt removed from 5' end and 2 nt removed from '3 end |
| 12 | 5'-TGACAACAAAGTTGGCCACCA-3' | 1 nt added to 5' end |
| 13 | 5'-GACAACAAAGTTGGCCACCAA-3' | 1 nt added to '3 end |
| 14 | 5'-G^AATTCGACAACAAAGTTGGCCACCA-3' | EcoRI site added to 5' end |

Additionally, one of skill in the art would envisage a genus of sequences substantially identical to SEQ ID NO: 2 wherein about one to about three nucleotides are added or removed from the 5' end and/or about one to about three nucleotides are added or removed from the 3' end, respectively, to include but not be limited to the following exemplary species:

| SEQ ID NO: | Sequence Substantially Identical to SEQ ID NO: 2 | Notes |
|---|---|---|
| 15 | 5'-TGGGACAACACCTGGAAC-3' | 2 nt removed from '3 end |
| 16 | 5'-GGACAACACCTGGAACAA-3' | 2 nt removed from 5' end |
| 17 | 5'-GGACAACACCTGGAAC-3' | 2 nt removed from 5' end and 2 nt removed from '3 end |
| 18 | 5'-GGGACAACACCTGGAACA-3' | 1 nt removed from 5' end and 1 nt removed from '3 end |
| 19 | 5'-GGGACAACACCTGGAACAA-3' | 1 nt removed from 5' end |
| 20 | 5'-TGGGACAACACCTGGAACA-3' | 1 nt removed from '3 end |
| 21 | 5'-GGACAACACCTGGAACA-3' | 2 nt removed from 5' end and 1 nt removed from '3 end |
| 22 | 5'-GGGACAACACCTGGAAC-3' | 1 nt removed from 5' end and 2 nt removed from '3 end |
| 23 | 5'-GTGGGACAACACCTGGAACAA-3' | 1 nt added to 5' end |
| 24 | 5'-TGGGACAACACCTGGAACAAG-3' | 1 nt added to '3 end |
| 25 | 5'-G^AATTCTGGGACAACACCTGGAACAA-3' | EcoRI site added to 5' end |

Finally, one of skill in the art would envisage a genus of sequences substantially identical to SEQ ID NO: 3 wherein about one to about three nucleotides are added or removed from the 5' end and/or about one to about three nucleotides are added or removed from the 3' end, respectively, to include but not be limited to the following exemplary species:

| SEQ ID NO: | Sequence Substantially Identical to SEQ ID NO: 3 | Notes |
|---|---|---|
| 26 | 5'-TTGGGTCCTGAGGCAACACT C-3' | 2 nt removed from '3 end |
| 27 | 5'-GGGTCCTGAGGCAACACTC GG-3' | 2 nt removed from 5' end |
| 28 | 5'-GGGTCCTGAGGCAACACTC-3' | 2 nt removed from 5' end and 2 nt removed from '3 end |
| 29 | 5'-TGGGTCCTGAGGCAACACT CG-3' | 1 nt removed from 5' end and 1 nt removed from '3 end |
| 30 | 5'-TGGGTCCTGAGGCAACACTC GG-3' | 1 nt removed from 5' end |
| 31 | 5'-TTGGGTCCTGAGGCAACAC TCG-3' | 1 nt removed from '3 end |
| 32 | 5'-GGGTCCTGAGGCAACACT CG-3' | 2 nt removed from 5' end and 1 nt removed from '3 end |
| 33 | 5'-TGGGTCCTGAGGCAACACTC-3' | 1 nt removed from 5' end and 2 nt removed from '3 end |
| 34 | 5'-GTTGGGTCCTGAGGCAACAC TCGG-3' | 1 nt added to 5' end |
| 35 | 5'-TTGGGTCCTGAGGCAACACTC GGA-3' | 1 nt added to '3 end |

The skilled artisan will also appreciate that oligonucleotide sequences substantially identical to SEQ ID NOs: 1-3 may differ from SEQ ID NOs: 1-3, respectively, with respect to the identity of at least one nucleotide base. However, all oligonucleotides sequences substantially identical to SEQ ID NOs: 1-3 will hybridize under stringent conditions (as defined herein) to all or a portion of the complements of SEQ ID NOs: 1-3 (i.e., target sequences), respectively. The terms "hybridize(s) specifically" or "specifically hybridize(s)" refer to complementary hybridization between an oligonucleotide (e.g., a primer or labeled probe) and a target sequence. The term specifically embraces minor mismatches that can be accommodated by reducing the stringency of the hybridization media to achieve the desired priming for the PCR polymerases or detection of hybridization signal.

Under stringent hybridization conditions, only highly complementary, i.e., substantially identical nucleic acid sequences, hybridize. Preferably, such conditions prevent hybridization of nucleic acids having 3 or more mismatches out of 20 contiguous nucleotides, more preferably 2 or more mismatches out of 20 contiguous nucleotides, most preferably one or more mismatch out of 20 contiguous nucleotides. The hybridizing portion of the hybridizing nucleic acid is at least about 90%, preferably at least about 95%, or most preferably about at least about 98%, identical to the sequence of a target sequence, or its complement.

Hybridization of a nucleic acid to a nucleic acid sample under stringent conditions is defined below. Nucleic acid duplex or hybrid stability is expressed as a melting temperature ($T_m$), which is the temperature at which the probe dissociates from the target DNA. This melting temperature is used to define the required stringency conditions. If sequences are to be identified that are substantially identical to the probe, rather than identical, then it is useful to first establish the lowest temperature at which only homologous hybridization occurs with a particular concentration of salt (e.g. SSC or SSPE). Then assuming that 1% mismatching results in a 1° C. decrease in $T_m$, the temperature of the final wash in the hybridization reaction is reduced accordingly (for example, if sequences having >95% identity with the probe are sought, the final wash temperature is decrease by 5° C.). In practice, the change in $T_m$ can be between 0.5° C. and 1.5° C. per 1% mismatch.

Stringent conditions involve hybridizing at 68° C. in 5×SSC/5× Denhart's solution/1.0% SDS, and washing in 0.2×SSC/0.1% SDS at room temperature. Moderately stringent conditions include washing in 3×SSC at 42° C. The parameters of salt concentration and temperature be varied to achieve optimal level of identity between the primer and the target nucleic acid. Additional guidance regarding such conditions is readily available in the art, for example, Sambrook, Fischer and Maniatis, Molecular Cloning, a laboratory manual, (2nd ed.), Cold Spring Harbor Laboratory Press, New York, (1989) and F. M. Ausubel et al eds., Current Protocols in Molecular Biology, John Wiley and Sons (1994).

The sequences 5'-CAACAAAGTTGGCCA-3' (SEQ ID NO: 36) and 5'-CATGACAACAAAGTTGGCCA-3' (SEQ ID NO: 37) are explicitly excluded as sequences substantially similar to SEQ ID NO: 1. Additionally, 5'-GGTGG-GACAACACCTGGAAC-3' (SEQ ID NO: 38), 5'-ACAA-CACCTGGA-3' (SEQ ID NO: 39), and 5'-CAACACCTGGAA-3' (SEQ ID NO: 40) are explicitly excluded as sequences substantially similar to SEQ ID NO: 2.

Another aspect of the invention relates to a kit for detecting MTB complex DNA having SEQ ID NOs: 1 and 2 or oligonucleotides substantially identical thereto. One embodiment of this aspect of the invention utilizes real-time PCR and includes SEQ ID NO: 3 or a oligonucleotides substantially identical thereto.

Another aspect of the invention relates to a method of detecting MTB complex DNA by using SEQ ID NOs: 1 and 2; or oligonucleotides substantially identical thereto, in a polymerase chain reaction performed on a biological sample.

The present methods and oligonucleotides can be applied to any type of biological sample that is suspected of containing MTB complex DNA. The term "biological sample" refers to a sample comprising any biological material (e.g., biological fluids or tissues) containing nucleic acids. Biological samples can include tissue samples, whole blood or serum, sputum, stool, urine, semen, pericardial fluid, nasopharyngeal/throat swabs, cerebrospinal fluid (CSF), amniotic fluid and the like. Alternatively, tissues may, for example, be surgically resected from a patient in the form of a biopsy or autopsy tissue sample. Preferably, at least about 50 mg of tissue is resected.

Most preferably, the tissue to be analyzed is in the form of, or contains a granuloma. Preferably, granulomas are aggregates of particular types of chronic inflammatory cells which form nodules in the millimeter size range. Granulomas may be confluent, forming larger areas. Granuloma have collections of modified macrophages, termed epithelioid cells, usually with a surrounding zone of lymphocytes. Epithelioid cells are so named by tradition because of their histological resemblance to epithelial cells, but are not in fact epithelial; they are derived from blood monocytes, like all macrophages. Epithelioid cells are less phagocytic than other macrophages and appear to be modified for secretory functions. Macrophages in granulomas are commonly further modified to form multinucleate giant cells. These arise by fusion of epithelioid macrophages without nuclear or cellular division forming huge single cells which may contain dozens of nuclei. In some circumstances the nuclei are arranged around the periphery of the cell, termed a Langhans-type giant cell (characteristically seen in tuberculosis); in other circumstances the nuclei are randomly scattered throughout the cytoplasm—for example in the foreign body type of giant cell which is formed in response to the presence of other indigestible foreign material in the tissue. Areas of granulomatous inflammation commonly undergo necrosis. The prototype example here is caseous necrosis in tuberculosis.

Generally microscale amounts of tissue are needed to detect MTB complex DNA. Preferably, a scrape of tissue from a pathological sample is used. More preferably, formalin-fixed and paraffin-embedded tissues are sectioned at a thickness of a 3 to 4 µm, and nucleic acids are isolated from a 0.2 cm by 0.2 cm area of the tissue section.

To amplify a target nucleic acid sequence in a sample by PCR, the sequence must be accessible to the components of the amplification system. In general, this accessibility is ensured by isolating the nucleic acids from the sample. A variety of techniques for extracting nucleic acids, in particular deoxyribonucleic acids, from biological samples are known in the art. Alternatively, if the sample is fairly readily disruptable, the nucleic acid need not be purified prior to amplification by the PCR technique, i.e., if the sample is comprised of cells, particularly peripheral blood lymphocytes or monocytes, lysis and dispersion of the intracellular components may be accomplished merely by suspending the cells in hypotonic buffer.

If it is not possible to extract DNA from the tissue sample soon after its resection, the sample may be fixed or frozen. DNA extracted and isolated from frozen or fresh samples of resected tissue is extracted by any method known in the art, for example, Sambrook, Fischer and Maniatis, Molecular Cloning, a laboratory manual, (2nd ed.), Cold Spring Harbor Laboratory Press, New York, (1989). Preferably, care is taken to avoid degradation of DNA during the extraction process.

Alternatively, tissue obtained from the patient may be fixed, preferably by formalin (formaldehyde) or gluteraldehyde treatment, for example. Biological samples fixed by alcohol immersion are also contemplated in the present invention. Fixed biological samples are often dehydrated and embedded in paraffin or other solid supports known to those of skill in the art. Such solid supports are envisioned to be removable with organic solvents, allowing for subsequent rehydration of preserved tissue. Fixed and paraffin-embedded (FPE) tissue specimen as described herein refers to storable or archival tissue samples.

DNA may be extracted from the FPE specimen by any of the methods as described in U.S. Pat. No. 6,428,963, which is hereby incorporated by reference in its entirety. Most preferably, total DNA is extracted from granulomas from a formalin-fixed and paraffin-embedded tissue specimen.

In an embodiment of the invention, DNA is isolated from an archival pathological sample or biopsy which is first deparaffinized. An exemplary deparaffinization method involves washing the paraffinized sample with an organic solvent, such as xylene. Deparaffinized samples can be rehydrated with an aqueous solution of a lower alcohol. Suitable lower alcohols, for example include, methanol, ethanol, propanols, and butanols. Deparaffinized samples may be rehydrated with successive washes with lower alcoholic solutions of decreasing concentration. Alternatively, the sample is simultaneously deparaffinized and rehydrated.

Once the sample is reyhdrated, DNA is extracted and isolated from the rehydrated tissue. Deparaffinized samples can be homogenized using mechanical, sonic or other means of homogenization, e.g. by laser microdisection. In one embodiment, rehydrated samples are homogenized in a solution comprising a chaotropic agent, such as guanidinium thiocyanate (also sold as guanidinium isothiocyanate).

Chaotropic agents include but not limited to: guanidinium compounds, urea, formamide, potassium iodiode, potassium thiocyantate and similar compounds. The preferred chaotropic agent for the methods of the invention is a guanidinium compound, such as guanidinium isothiocyanate (also sold as guanidinium thiocyanate) and guanidinium hydrochloride. Many anionic counterions are useful, and one of skill in the art can prepare many guanidinium salts with such appropriate anions. The effective concentration of guanidinium solution used in the invention generally has a concentration in the range of about 1 to about 5M with a preferred value of about 4M. If RNA is already in solution, the guanidinium solution may be of higher concentration such that the final concentration achieved in the sample is in the range of about 1 to about 5M. The guanidinium solution also is preferably buffered to a pH of about 3 to about 6, more preferably about 4, with a suitable biochemical buffer such as Tris-Cl. The chaotropic solution may also contain reducing agents, such as dithiothreitol (DTT), (β-mercaptoethanol; BME); and combinations thereof. The chaotropic solution may also contain RNAse and/or DNAase inhibitors.

Commercially available kits are also readily available to isolate nucleic acids from various tissues. For example, such kits are available from Qiagen, Inc. (Valencia, Calif.).

DNA is then recovered from the solution by, for example, phenol chloroform extraction, ion exchange chromatography or size-exclusion chromatography. DNA may then be further purified using the techniques of extraction, electrophoresis, chromatography, precipitation or other suitable techniques.

The amplification of MTB complex DNA from isolated total DNA from a fresh, frozen or fixed biological sample is preferably carried out using polymerase chain reaction (PCR) methods common in the art. The first step of each cycle of the PCR involves the separation of the nucleic acid duplex formed by the primer extension. Once the strands are separated, the next step in PCR involves hybridizing the separated strands with primers that flank the target sequence e.g. SEQ ID NOs: 1 and 2. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid. Strand separation is achieved by heating the reaction to a sufficiently high temperature for a sufficient time to cause the denaturation of the duplex but not to cause an irreversible denaturation of the polymerase (see U.S. Pat. No. 4,965,188). Template-dependent extension of primers in PCR is catalyzed by a polymerizing agent in the presence of adequate amounts of four deoxyribonucleoside triphosphates (typically dATP, dGTP, dCTP, dUTP and dTTP) in a reaction medium comprised of the appropriate salts, metal cations, and pH buffering system. Suitable polymerizing agents are enzymes known to catalyze template-dependent DNA synthesis. For example, *Thermus thermophilus* (Tth) DNA polymerase, a thermostable DNA polymerase by Roche Molecular Systems (Alameda, Calif.) PCR is most usually carried out as an automated process with a thermostable enzyme. In this process, the temperature of the reaction mixture is cycled through a denaturing region, a primer annealing region, and an extension reaction region automatically. Equipment specifically adapted for this purpose is commercially available from Roche Molecular Systems.

Most preferably, amplification of MTB complex DNA RNA is carried out using a fluorescence based real-time detection method (e.g. SmartCycler®, Cepheid, or the ABI PRISM 7700 or 7900 Sequence Detection System [TaqMan®], Applied Biosystems, Foster City, Calif.) or similar system as described by Heid et al., (Genome Res 1996; 6:986-994) and Gibson et al.(Genome Res 1996; 6:995-1001). This methodology is also referred to interchangeably herein as "real-time PCR" or "Q-PCR" where "Q" stands for quanitative. The output of the ABI 7700 (TaqMan® Instrument) is expressed in $C_T$'s or "cycle thresholds". A higher number of target molecules in a sample generates a signal with fewer PCR cycles (lower $C_T$) than a sample with a lower number of target molecules (higher $C_T$). By extension, given a set number of cycles, the level of fluorescence generated in the reaction will be indicative of the amount of amplification product which in turn, is a function of the amount template nucleic acid in the original biological sample. Therefore, real-time PCR also allows for the quantification of template DNA in the original biological sample. Preferably, the hydrolysis or TaqMan® probe for the oligonucleotide primer pair SEQ ID NO: 1 and 2, is SEQ ID NO: 3.

One of skill will recognize, however, that the oligonucleotides of the invention are useful for quantifying MTB complex DNA by any known method, such as ligase chain reaction (LCR) or self-sustained sequence replication, each of which provides sufficient amplification. Additionally, the present invention envisages the quantification of MTB DNA via use of a PCR-free system employing, for example fluorescent labeled probes similar to those of the Invader® Assay (Third Wave Technologies, Inc.).

As used herein, a "internal control DNA" is meant to include DNA whose presence in a biological sample enables an assessment of MTB complex DNA levels. Preferably, amplification of MTB complex DNA in a biological sample is conducted in parallel, i.e. at the same time, with amplification of internal control DNA. This allows for a determination of the overall amount of DNA in the sample and a control for variations in DNA recovery. "Internal controls" can include, but are not limited to the cyclophilin gene, β-actin gene, the transferrin receptor gene, GAPDH gene, and the like. Most preferably, the internal control DNA is a portion of the GAPDH gene.

Another aspect of the invention relates to a method of identifying compounds capable of inhibiting the growth of MTB complex pathogen. The method generally entails infecting a tissue culture with an MTB complex pathogen and then contacting a portion of the infected tissue culture with a compound suspected of being capable of inhibiting MTB complex pathogen growth. Next nucleic acids are isolated from the portion of the infected tissue culture contacted by the candidate compound. As a control, nucleic acids are also isolated from a portion of the remainder of the infected tissue culture not contacted by the candidate compound. Next, PCR is performed on both nucleic acid samples in parallel. Preferably, SEQ ID NO: 1 or an oligonucleotide substantially identical thereto is used as the forward primer and SEQ ID NO: 2 or an oligonucleotide substantially identical thereto is used as the reverse primer. A decrease in amplification product in the nucleic acid sample derived from the treated tissue culture relative to an amount of amplification product in the nucleic acid sample derived from the control indicates that a candidate compound is capable of inhibiting MTB complex pathogen growth. MTB complex pathogen may be cultured in MB/BacT bottle according to manufacturer instruction or on Loweinstein-Jensen (LJ) slants prepared media (Oxoid). More preferably, the tissue culture comprises the human alveolar epithelial cell line A549. Additionally, the term "tissue culture" as used herein is not limited to in vitro uses. The term also encompasses live animals that act as incubators for MTB complex pathogen growth such as suckling mice, rats or other mammals.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. The present invention may be practiced without some or all of these specific details. In other instances, well known process operations have not been described in detail, in order not to unnecessarily obscure the present invention. Accordingly, the drawings and description are to be regarded as illustrative in nature, and not as restrictive.

EXAMPLE 1

Mycobacterial DNA extraction procedure (Epicenter Technologies MasterPure Purification Kit Masidon, Wis.)

1. Control strains of mycobacteria were grown on LJ slants were fixed in 10% Formalin for at least 1 week before processing.
2. The formalin was then aspirated off using sterile plastic transfer pipettes into a 50 ml conical tube.
3. The slants were washed 3 times with sterile saline, each time the saline being transferred into 50 ml conical tubes.
4. The final aliquot of saline was added to the slant, and the organism growth was scraped from the surface and suspended in the saline.
5. The suspension was allowed to rest for at least 10 minutes to allow the larger particles to precipitate.
6. The remaining fluid containing the fixed mycobacteria was transferred to 2 ml conical tubes
7. The mycobacteria were allowed to settle out overnight.
8. Still under the biological safety cabinet, the saline was aspirated from the pellet and the solubilizing agent was added to the tubes. Each tube contained the following:
   a. 900 uL of 2× Tissue and Cell Lysis buffer
   b. 6 uL of Proteinase K (50 uG/mL)
9. The tubes were incubated for 20 minutes at 68° C., inverting the tubes twice during the heating process.
10. The tubes were chilled on ice for 5 minutes
11. 450 uL of MCP solution was added to each tube and the tubes vortexed
12. The tubes were then centrifuged in the microfuge
13. The supernatant was transferred into a clean microfuge tube 14. 500 uL of isopropanol was added to each tube and the tubes inverted 30-40 times
15. The tubes were frozen over night at −20° C.
16. The DNA was pelleted for 10 minutes in a microfuge
17. The DNA pellet was rinsed with 75% EtOH
18. The pellet was drained and dried thoroughly
19. The DNA was resuspended in 35 uL of TE Buffer The DNA was frozen at −20° C. until used for PCR amplification. Atypical (non-TB) mycobacterial strains used as negative controls:

*Mycobacterium marinum* ATCC 927
*M. avium* ATCC 25291
*M. cheloneae* ATCC 19233
*M. intracullulare* ATCC 13950
*M. kansasii* ATCC 12498
*M. fortuitum* ATCC 6841
*M. cheloneae* subspecies *abscessus* CDC strain from 2001
*M. terrae* UK strain from 1988
*M. gordonae* ATCC 14470

EXAMPLE 2

Design: Serial dilutions of formalin-fixed MTB complex DNA, other mycobacterial DNA and DNA from microdissected formalin-fixed paraffin-embedded tissue sections diagnosed as necrotizing granulomatous inflammation with acid-fast bacilli were used as templates for a PCR assay. Serial dilutions of fixed MTB complex DNA were prepared such that the highest dilution had only one copy of MTB complex DNA. The fixed tissue sections used were selected such that culture results were available for each case. Results of the real-time quantitative PCR assay using the primer pair SEQ ID NOs: 1 and 2 with the probe SEQ ID NO: 3, were correlated the culture results for the fixed tissue samples. GAPDH DNA was used as an internal control for the assay performed on the fixed tissue samples.

Results: All serial dilutions of MTB complex DNA were positive by this assay, including the highest dilution with only one copy of MTB complex DNA. FIG. 2. There was no cross reactivity with other mycobacterial or human DNA. FIG. 3. All cases positive for MTB by PCR on fixed tissue sections were also positive by culture. No MTB culture positive cases were missed by the assay. All cases negative for MTB by PCR on fixed tissue sections were also negative for the organism complex by culture. FIGS. 4 and 5.

Conclusion: The real-time quantitative PCR assay is rapid, specific and highly sensitive for identification of MTB in formalin-fixed paraffin-embedded tissue sections. It is technically simple and can be used in routine pathology practice.

In this disclosure there is described only the preferred embodiments of the invention and but a few examples of its versatility. It is to be understood that the invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances and procedures described herein. Such equivalents are considered to be within the scope of this invention.

What is claimed is:

1. An isolated oligonucleotide consisting of SEQ ID NO: 1.

2. An isolated oligonucleotide consisting of SEQ ID NO: 2.

3. An isolated oligonucleotide consisting of SEQ ID NO: 42, wherein the oligonucleotide is capable of amplifying MTB complex DNA when used in conjunction with SEQ ID NO: 1 in a polymerase chain reaction.

4. An isolated oligonucleotide capable of being a hydrolysis probe for the oligonucleotide primer pair of SEQ ID NOs: 1 and 2, wherein said oligonucleotide consists of the sequence of SEQ ID NO: 3 or SEQ ID NO: 43.

5. A kit for detecting MTB complex DNA comprising a first isolated oligonucleotide consisting of SEQ ID NO: 1 and a second oligonucleotide selected from an oligonucleotide consisting essentially SEQ ID NO: 41 or SEQ ID NO: 42.

6. A kit for detecting MTB complex DNA comprising a first isolated oligonucleotide consisting of SEQ ID NO: 2 and a second oligonucleotide selected from an oligonucleotide consisting essentially of SEQ ID NO: 41 or SEQ ID NO: 43.

7. A kit for detecting MTB complex DNA comprising a first isolated oligonucleotide consisting of SEQ ID NO: 1 and a second oligonucleotide consisting of SEQ ID NO: 2.

8. A kit for detecting MTB complex DNA comprising a first oligonucleotide selected from the group consisting of:

(A) an isolated oligonucleotide consisting of the sequence SEQ ID NO: 1;

(B) and a second oligonucleotide selected from the group consisting of:

1. an isolated oligonucleotide consisting of SEQ ID NO: 2;

2. an isolated oligonucleotide consisting of 14 to 26 nucleotides, wherein said oligonucleotide hybridizes the complement of a sequence consisting of SEQ ID NO: 2 under stringent conditions, wherein said oligonucleotide is capable of amplifying MTB complex DNA when used in conjunction with SEQ ID NO: 1 in a polymerase chain reaction; and 3. an isolated oligonucleotide consisting of SEQ ID NO: 42, and wherein the oligonucleotide is capable of amplifying MTB complex DNA when used in conjunction with SEQ ID NO: 1 in a polymerase chain reaction.

9. The kit of claims 7 or 8 further comprising a third isolated oligonucleotide consisting of SEQ ID NO: 3 or SEQ ID NO: 43.

10. The kit of claims 7 or 8 further comprising a PCR reaction buffer and DNA polymerase enzyme.

* * * * *